United States Patent [19]
Casica et al.

[11] Patent Number: 5,702,270
[45] Date of Patent: Dec. 30, 1997

[54] SURGICAL HANDPIECE HOLDER

[75] Inventors: Peter D. Casica, San Juan Capistrano; James Y. Chon, Chino Hills, both of Calif.

[73] Assignee: Alcon Laboratories, Inc., Fort Worth, Tex.

[21] Appl. No.: 572,486

[22] Filed: Dec. 14, 1995

[51] Int. Cl.$^6$ .................................................. H01R 13/60
[52] U.S. Cl. .......................... 439/528; 439/909; 24/339
[58] Field of Search ...................... 24/339, 335, 115 M; 439/929, 529, 501, 528, 909

[56] References Cited

U.S. PATENT DOCUMENTS

| | | | |
|---|---|---|---|
| 3,589,363 | 6/1971 | Banko et al. | |
| 3,986,648 | 10/1976 | Antonini et al. | 219/242 |
| 4,223,676 | 9/1980 | Wuchinich et al. | |
| 4,246,902 | 1/1981 | Martinez | |
| 4,493,694 | 1/1985 | Wuchinich | |
| 4,515,583 | 5/1985 | Sorich | |
| 4,577,755 | 3/1986 | Ramsay | 206/370 |
| 4,589,415 | 5/1986 | Haaga | |
| 4,609,368 | 9/1986 | Dotson, Jr. | 604/22 |
| 4,869,715 | 9/1989 | Sherburne | 604/22 |
| 4,911,159 | 3/1990 | Johnson et al. | 606/37 |
| 4,921,444 | 5/1990 | Cama | 439/528 |
| 4,922,902 | 5/1990 | Wuchinich et al. | 604/22 |
| 5,138,351 | 8/1992 | Wiegand et al. | 354/81 |
| 5,159,774 | 11/1992 | Bennis et al. | 24/339 |
| 5,265,840 | 11/1993 | Gillespie et al. | 251/4 |
| 5,339,498 | 8/1994 | Parsons | 24/115 M |
| 5,431,664 | 7/1995 | Ureche et al. | 604/22 |
| 5,447,253 | 9/1995 | Graber | 211/70.6 |

FOREIGN PATENT DOCUMENTS

| | | |
|---|---|---|
| 0 633 011 A1 | 1/1995 | European Pat. Off. |
| 2638617 | 3/1978 | Germany ............ 439/528 |
| G 93 06 851.4 | 11/1993 | Germany |

*Primary Examiner*—Gary F. Paumen
*Attorney, Agent, or Firm*—Michael C. Mayo; Jeffrey S. Schira

[57] ABSTRACT

A surgical handpiece holder for use in protecting a surgical handpiece during storage or autoclaving, and providing a template for the storage of excess handpiece wire is disclosed.

15 Claims, 8 Drawing Sheets

SURGICAL HANDPIECE HOLDER

BACKGROUND OF THE INVENTION

The present invention relates to ultrasonic surgical equipment and, in particular, to holders used to protect handpiece instruments from damage. Ultrasonic handpieces are critical and principal parts of ultrasonic surgical equipment.

A typical ultrasonic surgical device suitable for ophthalmic procedures consists of an ultrasonically driven handpiece, an attached cutting tip, an irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezo-electric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced-diameter portion or cone at the body's distal end. The nosecone is externally threaded to accept the irrigation sleeve. Likewise, the horn bore is internally threaded at its distal end to receive the external thread of the cutting tip. The irrigation sleeve also has an internally threaded bore that is screwed onto the external threads of the cone. The cutting tip is adjusted so that the tip projects only a predetermined amount past the open end of the irrigating sleeve. Ultrasonic handpieces and cutting tips are more fully described in U.S. Pat. Nos. 3,589,363, 4,223,676, 4,246,902, 4,493,694, 4,515,583, 4,589,415, 4,609,368, 4,869,715, 4,922,902 and 5,431,664, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device on the console. The aspiration of emulsified tissue is aided by a saline flushing solution or irrigant that is injected into the surgical site through the small annular gap between the inside surface of the irrigating sleeve and the cutting tip.

The improper care of these delicate handpiece instruments can result in damage to the instrument. The piezo-electric horns used in ultrasonic handpieces must be carefully tuned to assure that all of the movement of the horn is in the longitudinal direction and that the node of maximum longitudinal displacement occurs at the distal end of the cutting tip. If the handpiece is handled roughly or dropped, the piezo-electric horns may become grossly out of tune thereby necessitating replacement. Likewise, as described above, the cutting tip end of the handpiece comprises an internally-threaded titanium horn, sheathed by an open nosecone. If the instrument is handled roughly or dropped, the nosecone or horn can be bent such that the horn can no longer deliver maximum vibrational energy to the cutting tip, or the cutting tip may no longer be able to be screwed into the horn, thereby requiring replacement.

Another problem is that handpieces usually require a lengthy electrical cord because the console to which the handpiece is connected generally is some distance away from the surgical site. Due to this distance, the cord is not easily managed when the handpiece is stored or when the handpiece is autoclaved. For example, the cord can get caught on various parts of the surgeon's tray, stepped on, or even damaged by getting caught in the autoclave door.

A need, therefore, exists for a device that will help prevent damage to delicate handpieces.

SUMMARY OF THE INVENTION

The present invention is a handpiece holder for the compact storage of a handpiece-wire assembly. The invention comprises a body having a scabbard, an electrical connector housing and a bridge. The housing receives the handpiece electrical console connector and wire. The scabbard receives the handpiece when not in use. The bridge provides a winding point around which excess wire of the handpiece may be wrapped for storage. The holder helps prevent damage to the handpiece during non-surgical handling and sterilization.

Accordingly, one objective of the present invention is to provide a surgical handpiece holder for the protection of the handpiece during storage and sterilization.

Another objective of the present invention is to provide a surgical handpiece holder having a winding point around which excess wire from the handpiece may be wrapped.

DETAILED DESCRIPTION OF THE INVENTION

Figure 1:
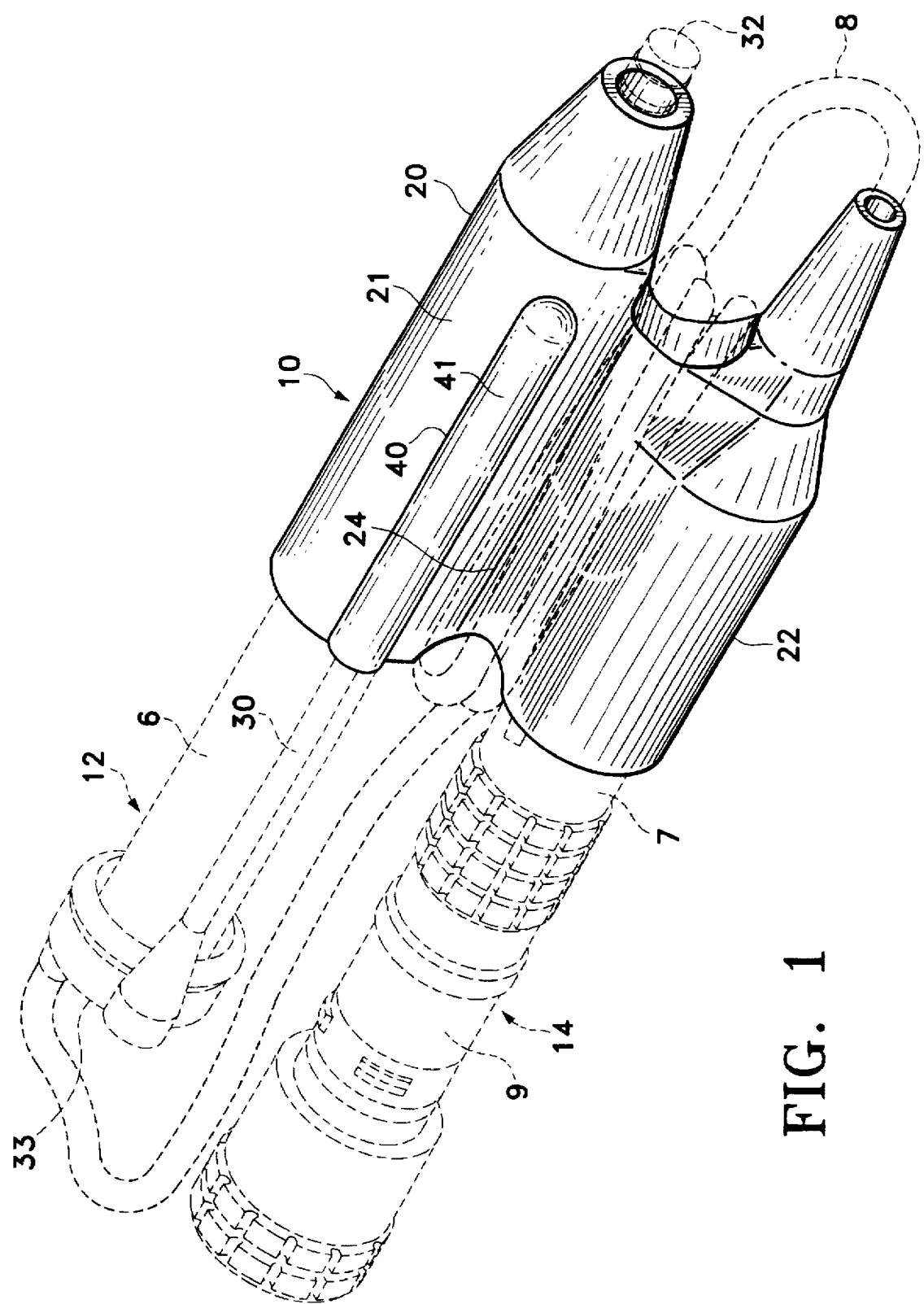
FIG. 1 is a perspective view of the handpiece holder of the present invention.
Figure 2:
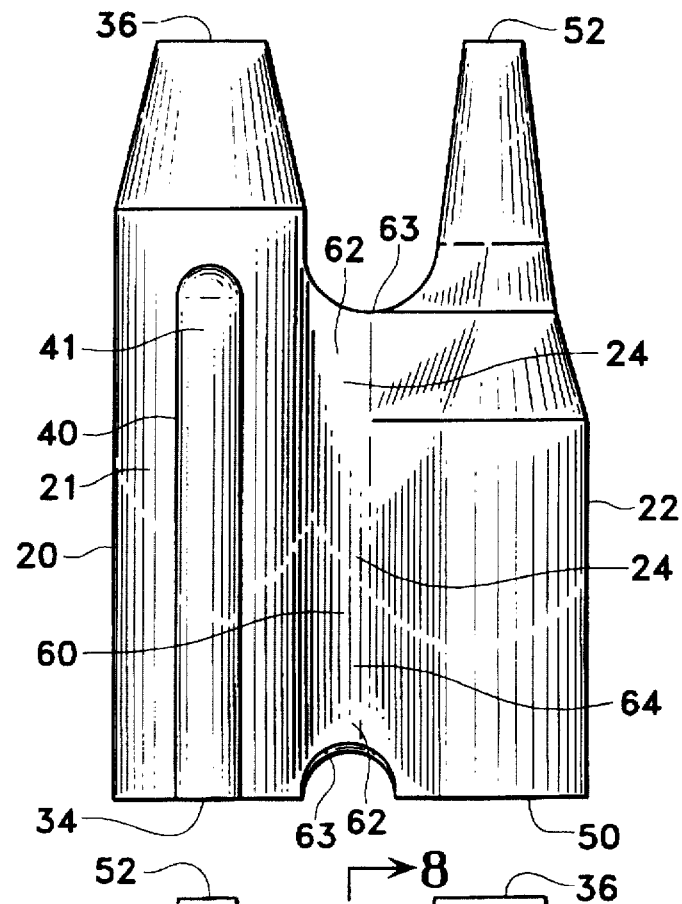
FIG. 2 is a top plan view of the present invention.

As illustrated in FIGS. 1 and 2, handpiece holder 10 of the present invention includes scabbard 20, electrical connector housing 22 and bridge 24.

Figure 8:
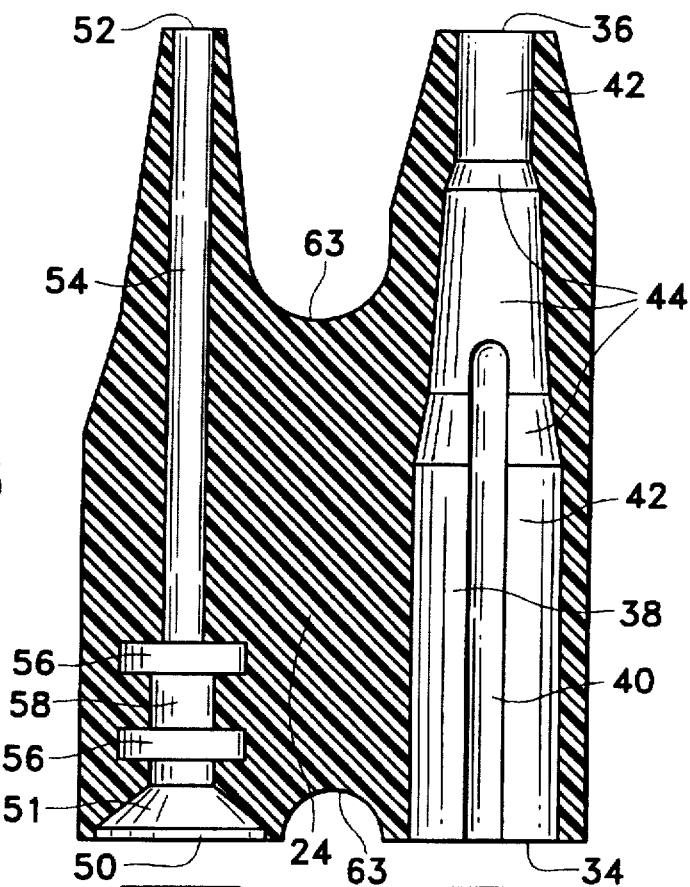
FIG. 8 is a cross-sectional view of line 8—8 of FIG. 3 of the present invention.

Scabbard 20 includes large open end 34, small open end 36, bore 38 and channel 40 (FIGS. 1, 2 and 8). Bore 38 may be any cross-sectional shape suitable for receiving handpiece 12, such as a continuously reduced diameter bore running from large open end 34 to small open end 36. As illustrated in FIG. 8, bore 38 preferably may be formed by a plurality of larger and smaller diameter cylindrical bores 42, and larger and smaller conic bores 44. Channel 40 protrudes on exterior 21 of scabbard 20, forming raised ridge 41 and communicating with bore 38.

Electrical connector housing 22 includes large open end 50, small open end 52 and bore 54 (FIGS. 1, 2 and 8). Bore 54 runs coaxially along the longitudinal axis of housing 22, and communicates with open ends 50 and 52. Enlarged portion 58 of bore 54 is interposed between grooves 56 and counterbore 51 of open end 50. Grooves 56 communicate with bore 54, and provide a bend relief for the attachment of flexible wire 8, as discussed below.

Figure 3:
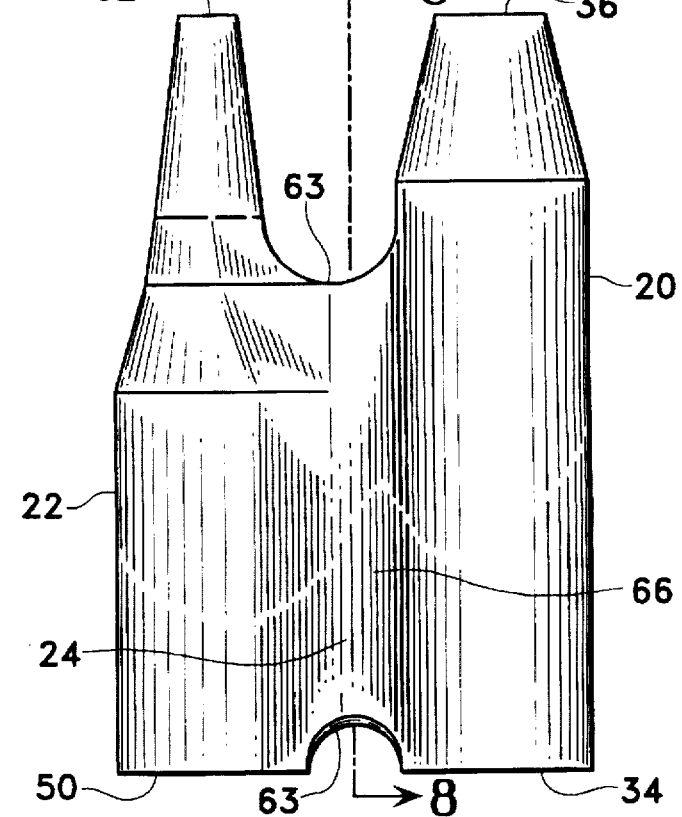
FIG. 3 is bottom plan view of the present invention.
Figure 4:
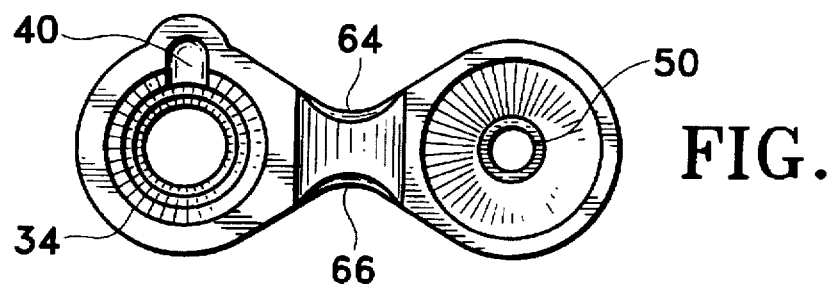
FIG. 4 is rear elevational view of the present invention.
Figure 5:
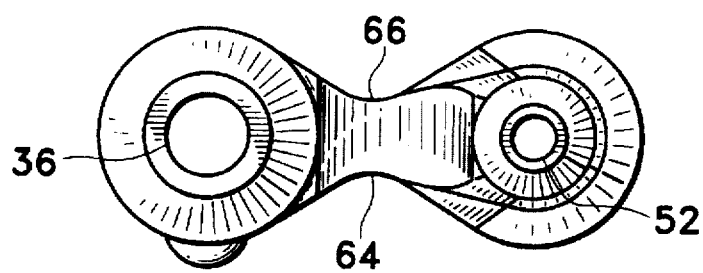
FIG. 5 is a front elevational view of the present invention.
Figure 6:
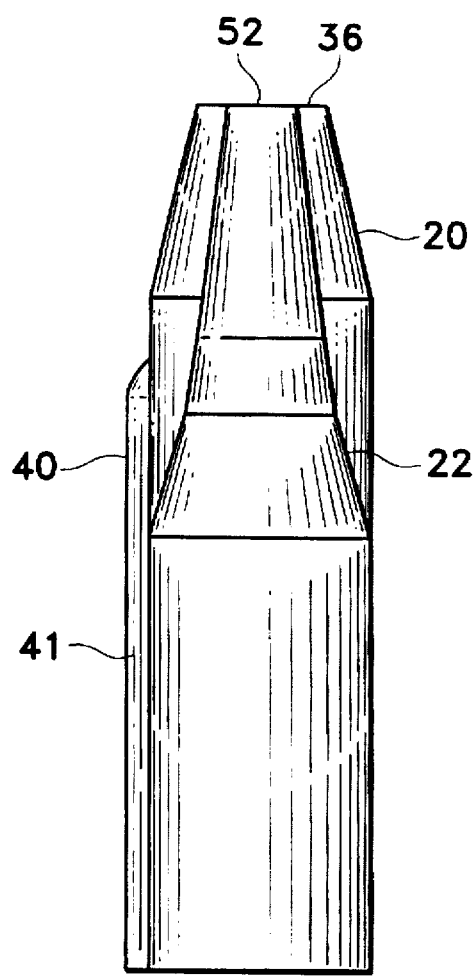
FIG. 6 is a first side view of the present invention.
Figure 7:
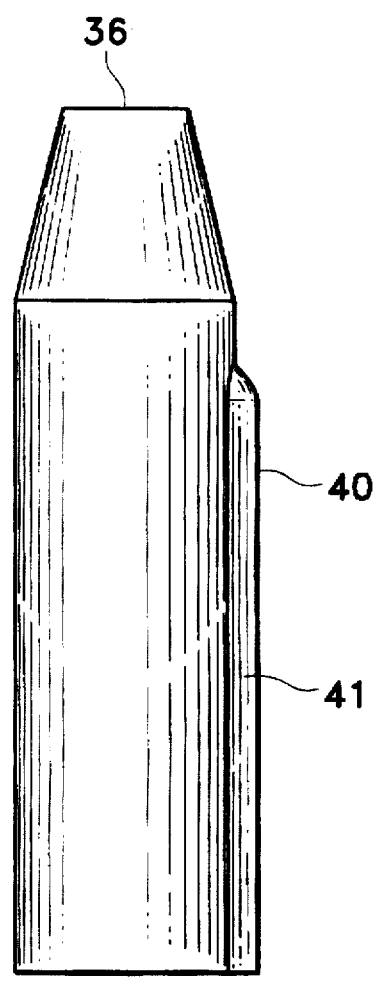
FIG. 7 is the opposite side view of the present invention.

Scabbard 20 and housing 22 are held in spaced relationship by bridge 24. Bridge 24 generally consists of longitudinal body 60 having ends 62, front side 64 and back side 66. Sides 64 and 66 preferably are concave (FIGS. 1, 4 and 5). Ends 62 preferably form semi-circle slots 63, as best illustrated in FIGS. 3 and 8.

Holder 10 preferably is formed of an autoclavable plastic such as PVC, polypropylene, polysulfone, polyetherimide or autoclavable rubber such as isoprene or silicone, and as one piece by injection molding, but other suitable materials and molding techniques may also be used. Alternatively, holder 10 may be assembled by fusing scabbard 20 and housing 22 to bridge 24 by gluing, thermo-bonding or other mechanical means known to those skilled in the art.

Figure 13:
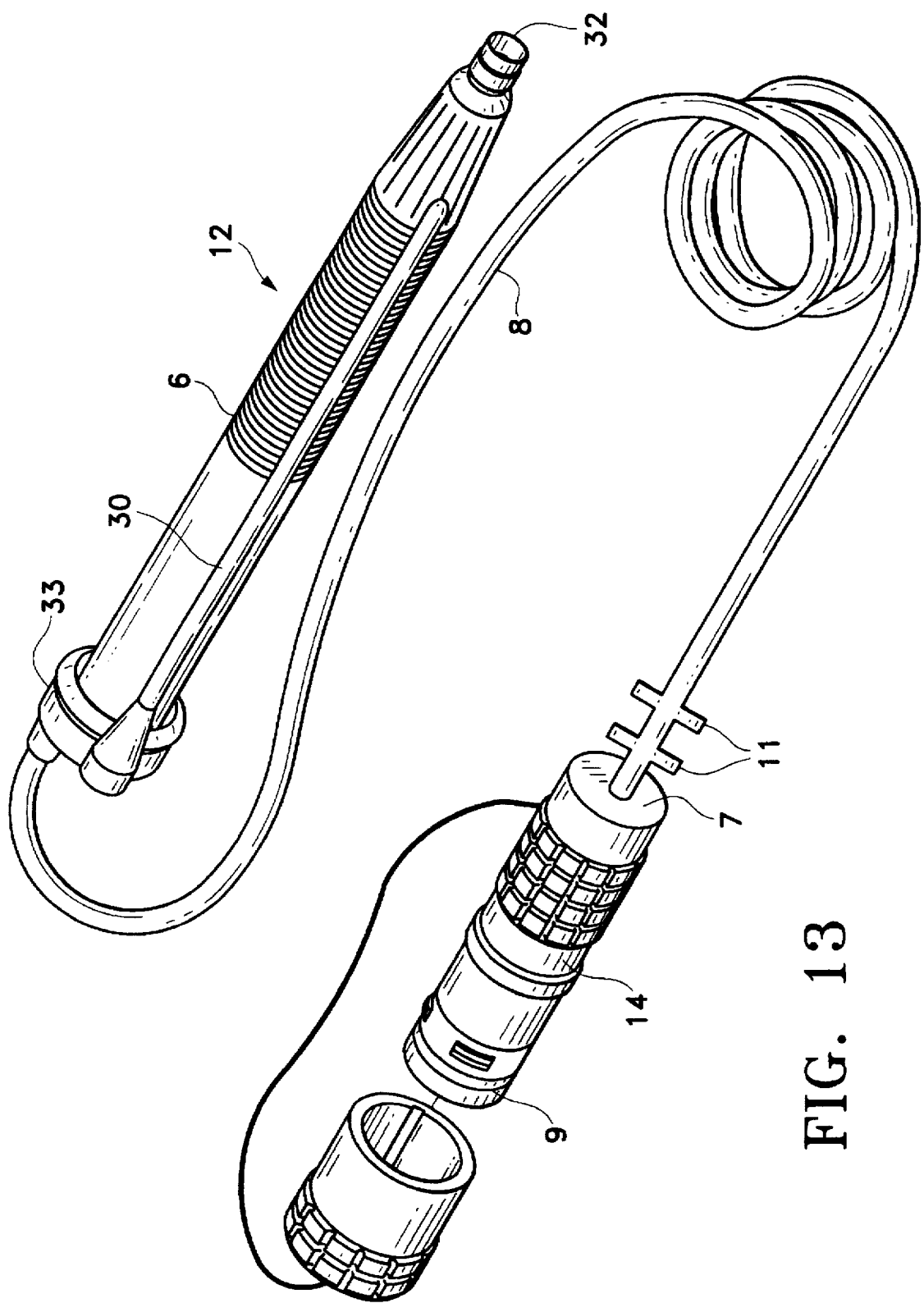
FIG. 13 is a perspective view of a handpiece to be used with the present invention, but not forming a part of the present invention.

As illustrated in FIGS. 1 and 13, handpiece 12 may be any commercially available surgical handpiece, including I/A handpieces, cautery handpieces or phacoemulsification handpieces, and generally includes body 6, irrigation tube 30, wire 8 and electrical connector 14. Body 6 has cutting tip end 32 and wire end 33. Connector 14 includes wire end 7 and connector end 9. Irrigation tube 30 is disposed longitudinally on body 6. Wire 8 has ribs 11 and is connected between end 33 of body 6 and wire end 7 of connector 14.

Figure 11:
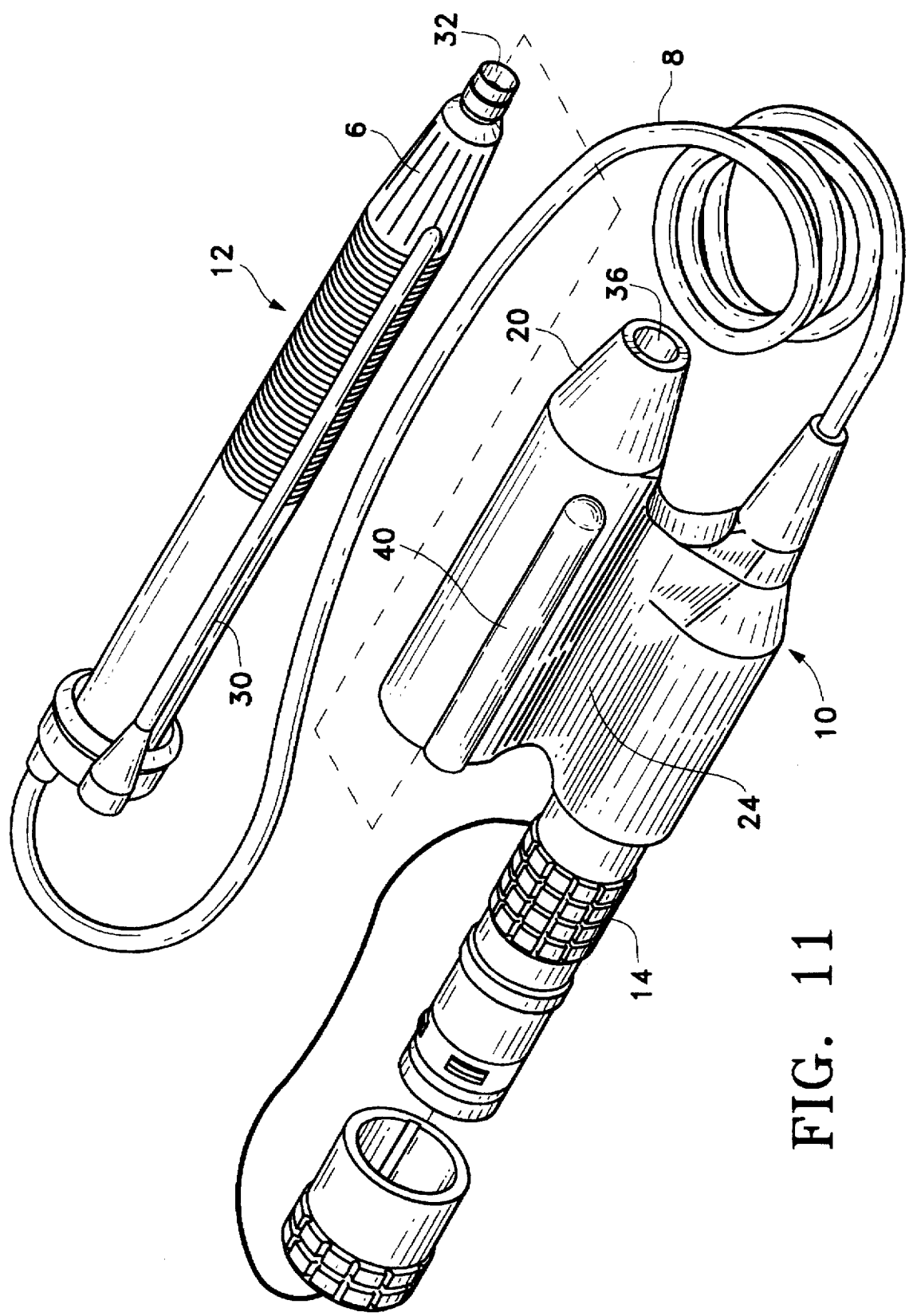
FIG. 11 is an exploded perspective view of the present invention with a handpiece instrument.
Figure 12:
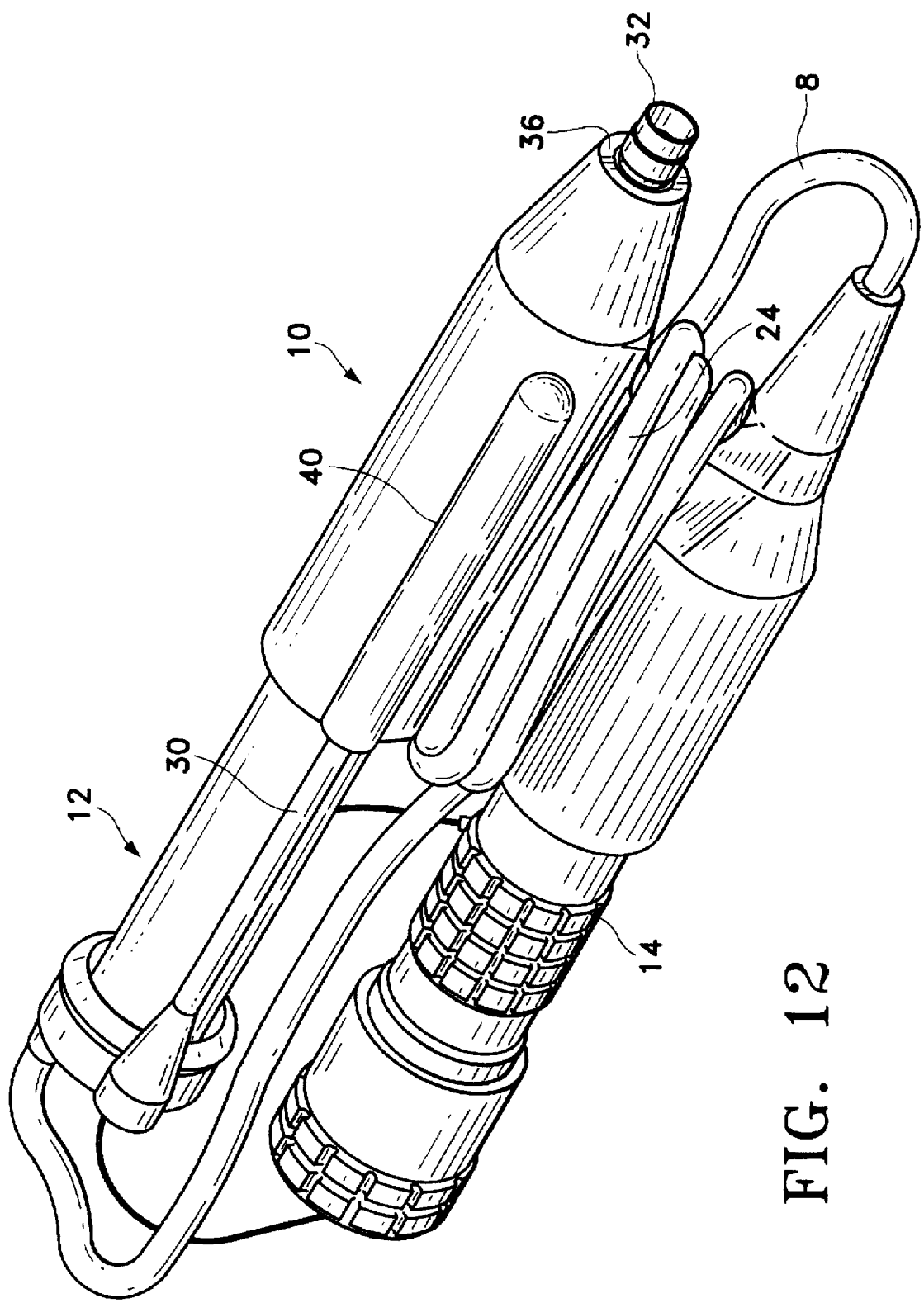
FIG. 12 is a perspective view of the present invention in operation with a handpiece instrument.

In operation, a portion of wire end 7 of connector 14 is received within counterbore 51 of housing 22. Ribs 11 of wire 8 are pulled through enlarged bore 58 such that ribs 11 are seated in grooves 56, and wire 8 runs through bore 54 and out of end 52. More preferably, wire 8 and connector 14 are placed in an injection mold and housing 22 is then molded around connector 14, wire 8 and ribs 11, thereby fixing connector 14 at end 50, ribs 11 within grooves 56, and wire 8 within bore 54. Handpiece body 6 is inserted through open end 34 of scabbard 20 so that irrigation tube 30 is guided into channel 40 and cutting tip end 32 of body 6 protrudes from open end 36 of scabbard 20 (FIG. 11). Wire 8 may then be wrapped around bridge 24. Alternatively, wire 8 is first wrapped in a plurality of revolutions around bridge 24 and then handpiece body 6 is inserted in scabbard 20 as described above (FIG. 12).

Figure 10:
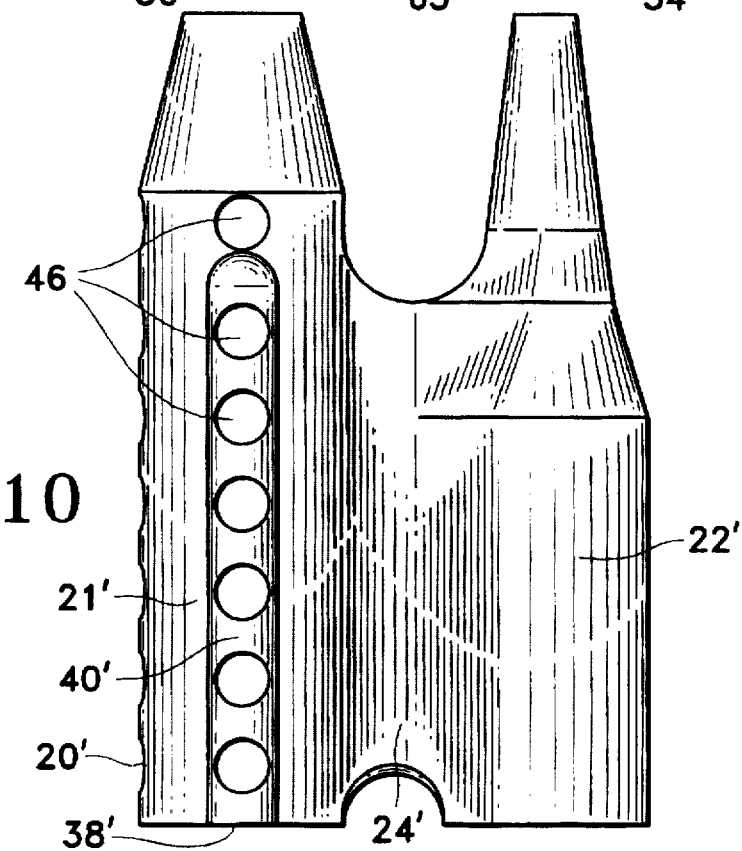
FIG. 10 is a top plan view of a second embodiment of the present invention.
Figure 9:
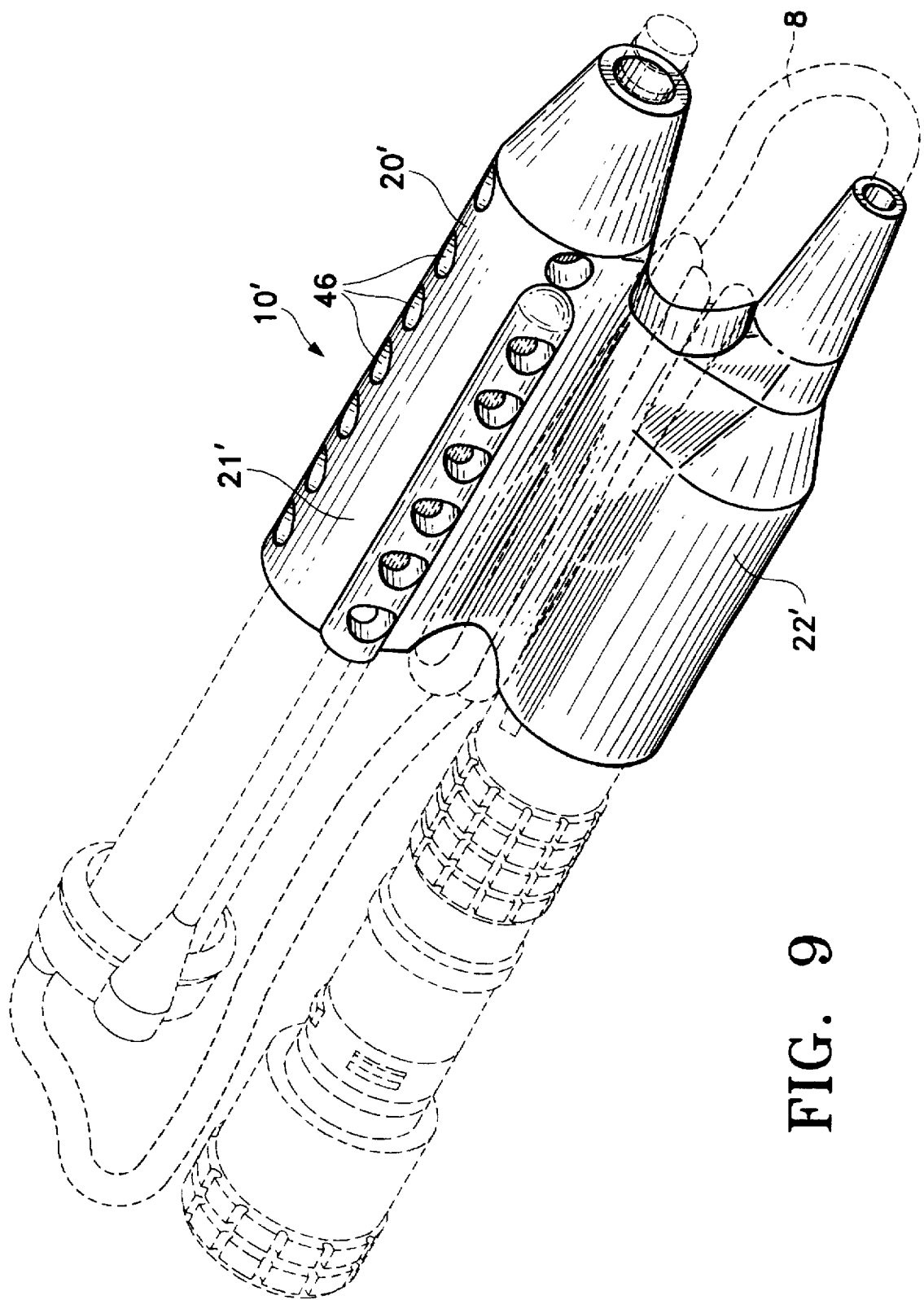
FIG. 9 is a perspective view of a second embodiment of the present invention.

As illustrated in FIGS. 9 and 10 in a second embodiment of the present invention, scabbard 20' is ventilated by a plurality of holes 46 running from exterior 21' to bore 38' of scabbard 20'. Holes 46 allow air to communicate freely with bore 38', thereby allowing for a greater penetration of steam during autoclaving. Holes 46 may be any suitable size, shape and number. Preferably, the holes will be generally from about 0.125 to 0.188 inches in diameter and be arranged in 3 columns of 7 holes, uniformly positioned about the longitudinal axis of scabbard 20'.

This description is given for purposes of illustration and explanation. It will be apparent to those skilled in the relevant art that changes and modifications may be made to the invention described above without departing from its scope or spirit.

What is claimed is:

1. A surgical handpiece holder comprising:
    (a) a scabbard having a first longitudinal bore, the first longitudinal bore being sized and shaped to receive a surgical handpiece;
    (b) an electrical connector housing having a second longitudinal bore, the second longitudinal bore having at least one annular groove; and
    (c) a bridge, generally concave in transverse cross-section shorter in length than the scabbard and the electrical connector housing and being longitudinally disposed between the scabbard and the housing.

2. The handpiece holder of claim 1, wherein the scabbard further comprises an exterior surface having a plurality of holes running from the exterior surface to the bore.

3. The handpiece holder of claim 1, wherein the holder comprises plastic or rubber.

4. The handpiece holder of claim 2, wherein the holder comprises plastic or rubber.

5. A combination surgical handpiece and holder, comprising:
    (a) a surgical handpiece comprising a body having a cutting tip end and a back wire end, an electrical wire, and an electrical connector having a connector end and a wire end, wherein the wire is disposed between the back wire end of the body and the wire end of the connector;
    (b) a holder comprising a scabbard having a first longitudinal bore, the first longitudinal bore being sized and shaped to receive the cutting tip end of the surgical handpiece, an electrical connector housing having a large open end, a small open end and a second longitudinal bore communicating with the large and small open ends, and a bridge being longitudinally disposed between the scabbard and housing;
    wherein the cutting tip end of the handpiece body may be received within the first longitudinal bore of the scabbard, the connector is received at least partially within the large open end of the connector housing, the wire runs from the connector through the second longitudinal bore of the connector housing and out the small open end of the housing, wherein any excess wire may be wrapped longitudinally around the bridge.

6. The apparatus of claim 5, wherein the scabbard further comprises an exterior surface having a plurality of holes running from the exterior surface to the first longitudinal bore, and the bridge is generally concave in transverse cross-section.

7. The apparatus of claim 5, wherein the holder comprises plastic or rubber.

8. The apparatus of claim 6, wherein the holder comprises plastic or rubber.

9. A method of protecting a surgical handpiece, the handpiece having a body and an electrical connector, the body and the connector communicating through a wire, which comprises the steps of:
    (a) providing a handpiece holder, the holder comprising a scabbard having a longitudinal bore, the longitudinal bore being sized and shaped to receive a cutting tip end of the body of the handpiece, an electrical connector housing, and a bridge being longitudinally disposed between the scabbard and the housing;
    (b) inserting the cutting tip end of the handpiece within the longitudinal bore of the scabbard; and (c) inserting the connector at least partially within the connector housing.

10. The method of claim 9, wherein the holder comprises plastic or rubber.

11. The method of claim 9, wherein the housing further comprises a large open end, a small open end and a longitudinal bore communicating with the large and small open ends.

12. The method of claim 11, wherein any excess wire from the handpiece is wrapped longitudinally around the bridge.

13. The method of claim 12, wherein the holder comprises plastic or rubber.

14. The method of claim 9, wherein the scabbard further comprises an exterior surface having a plurality of holes running from the exterior surface to the longitudinal bore, and the bridge is generally concave in transverse cross-section.

15. The method of claim 14, wherein the holder comprises plastic or rubber.

* * * * *